(12) United States Patent
Shire

(10) Patent No.: US 11,946,918 B2
(45) Date of Patent: Apr. 2, 2024

(54) METHOD FOR CALIBRATING AT LEAST ONE SENSOR BY USE OF AT LEAST ONE CALIBRATION SENSOR

(71) Applicant: VOLVO TRUCK CORPORATION, Gothenburg (SE)

(72) Inventor: Joshua Shire, Gothenburg (SE)

(73) Assignee: VOLVO TRUCK CORPORATION, Gothenburg (SE)

( * ) Notice: Subject to any disclaimer, the term of this patent is extended or adjusted under 35 U.S.C. 154(b) by 174 days.

(21) Appl. No.: 17/647,538

(22) Filed: Jan. 10, 2022

(65) Prior Publication Data

US 2022/0252563 A1 Aug. 11, 2022

(30) Foreign Application Priority Data

Feb. 10, 2021 (EP) ..................................... 21156156

(51) Int. Cl.
*G01N 33/00* (2006.01)
*B60W 50/06* (2006.01)
(Continued)

(52) U.S. Cl.
CPC ......... *G01N 33/0006* (2013.01); *B60W 50/06* (2013.01); *G01S 19/01* (2013.01); *H04W 4/40* (2018.02)

(58) Field of Classification Search
CPC ......... H04W 4/40; G01S 19/01; B60W 50/06; G01N 33/0006
(Continued)

(56) References Cited

U.S. PATENT DOCUMENTS

2009/0172035 A1* 7/2009 Lessing .................. G06Q 30/02
2011/0163892 A1* 7/2011 Groves .............. G01N 33/0075
340/901

(Continued)

FOREIGN PATENT DOCUMENTS

WO 2017189361 A1 11/2017
WO WO-2017189361 A1 * 11/2017

OTHER PUBLICATIONS

European Search Report dated Jul. 28, 2021 in corresponding European Patent Application No. 21156156.8, 8 pages.

*Primary Examiner* — Yazan A Soofi
(74) *Attorney, Agent, or Firm* — Venable LLP; Jeffri A. Kaminski

(57) ABSTRACT

A method for calibrating at least one sensor by use of at least one calibration sensor, the method comprising: obtaining information indicative of a proximity time period when the at least one sensor and the at least one calibration sensor are in a predefined proximity zone of each other for a time period which is sufficient for calibration; obtaining information about a refractory time period for at least one of the at least one sensor and the at least one calibration sensor; calibrating the at least one sensor by a sensor reading of the at least one sensor and a sensor reading of the at least one calibration sensor, which sensor readings are taken when they are in the predefined proximity zone, wherein the refractory time period for the at least one of the at least one sensor and the at least one calibration sensor is considered by delaying its sensor reading such that it is ensured that the sensor readings of the at least one sensor and the at least one calibration sensor are spatially and temporally aligned for the calibration.

15 Claims, 2 Drawing Sheets

(51) Int. Cl.
  *G01S 19/01* (2010.01)
  *H04W 4/40* (2018.01)
(58) Field of Classification Search
  USPC .......................................................... 701/514
  See application file for complete search history.

(56) References Cited

U.S. PATENT DOCUMENTS

| | | | |
|---|---|---|---|
| 2018/0203481 A1* | 7/2018 | Chen | G01D 9/285 |
| 2019/0236862 A1* | 8/2019 | Mercep | G08G 1/165 |
| 2020/0110065 A1* | 4/2020 | Borrel | G01N 33/0006 |
| 2020/0226790 A1 | 7/2020 | Alvarez et al. | |
| 2020/0264275 A1 | 8/2020 | Voorheis et al. | |
| 2020/0371530 A1* | 11/2020 | Anderson | H04W 4/40 |
| 2021/0047050 A1* | 2/2021 | Coenen | B64D 47/06 |
| 2021/0063165 A1* | 3/2021 | Mercep | G01C 21/30 |
| 2023/0243678 A1* | 8/2023 | Shire | G01D 21/00 |
| | | | 702/188 |
| 2023/0266079 A1* | 8/2023 | Ishmael | C09K 5/066 |
| | | | 165/47 |

\* cited by examiner

METHOD FOR CALIBRATING AT LEAST ONE SENSOR BY USE OF AT LEAST ONE CALIBRATION SENSOR

TECHNICAL FIELD

The invention relates to a method for calibrating at least one sensor by use of at least one calibration sensor. The invention also relates to a system and to a first and/or second vehicle.

The invention can be applied in heavy-duty vehicles, such as trucks, buses and construction equipment. Although the invention will be described with respect to a bus, the invention is not restricted to this particular vehicle, but may also be used in other vehicles such as passenger cars, trucks, construction equipment, such as wheel loaders, excavators etc., marine vessels and aircraft, such as drones etc.

BACKGROUND

Vehicles may be equipped with sensors for measuring different ambient conditions. For example, it is well-known to measure the ambient temperature during driving. In addition, it is also known to measure other environmentally related properties, such as properties relating to the ambient air quality. Such sensors may for example measure the level of $NO_x$ (Nitrogen oxides), $CO_2$ (carbon dioxide) and particle levels in the ambient air.

The above-mentioned sensors are thus adapted to move during use, i.e. the sensors are moved with the vehicle while the vehicle is moving.

The present invention relates to such moving sensors and to any other types of moving sensors. In particular, the present invention relates to sensors which are movable and which also would benefit from being calibrated during use.

SUMMARY

In view of the above, an object of the invention is to provide an improved method for calibrating at least one sensor. In addition, an object of the invention is to provide an improved system and/or an improved vehicle.

According to a first aspect of the invention, the object is achieved by a method according to claim 1. Thus, a method for calibrating at least one sensor by use of at least one calibration sensor is provided, wherein the at least one sensor and the at least one calibration sensor are moving relative each other during calibration. The method comprises:

obtaining information indicative of a proximity time period when the at least one sensor and the at least one calibration sensor are and/or will be in a predefined proximity zone of each other for a time period which is sufficient for calibration;

obtaining information about a refractory time period for at least one of the at least one sensor and the at least one calibration sensor, the refractory time period defining a time period between two consecutive sensor readings in which the sensor is unable to take a sensor reading;

calibrating the at least one sensor by a sensor reading of the at least one sensor and a sensor reading of the at least one calibration sensor, which sensor readings are taken when they are in the predefined proximity zone, wherein the refractory time period for the at least one of the at least one sensor and the at least one calibration sensor is considered by delaying its sensor reading such that it is ensured that the sensor readings of the at least one sensor and the at least one calibration sensor are spatially and temporally aligned for the calibration.

By the provision of the present invention as disclosed herein, a more accurate, reliable and robust calibration of the at least one sensor is achieved. In particular, the present invention is based on a realization that it may be important to consider the refractory time period for the calibration. The refractory time period, which also may be denoted a recovery time period, is the time period after a sensor reading when the sensor cannot initiate another sensor reading, or at least when it cannot reliably perform another sensor reading. The refractory time period may therefore be a time period when a sensor is not functioning at all or when it is not functioning with a sufficient reliability. As such, the calibration can be improved by delaying a sensor reading with respect to the refractory time period such that the at least one sensor and the at least one calibration sensor are spatially and temporally aligned for the calibration. In contrast, if not considering the refractory time period as disclosed herein, the calibration may not be properly performed. In addition, by not considering the refractory time period, an opportunity to calibrate the at least one sensor may be missed. It has namely also been realized that the time period which is sufficient for calibration may be very short for moving sensors, and therefore it may be of utmost importance that that sensors involved in the calibration are available and able to take at least one sensor reading during the short time period when the sensors are close enough to each other.

A "predefined proximity zone" as used herein may refer to an area or space which is defined by a maximum allowed distance between the at least one sensor and the at least one calibration sensor. The area or space may e.g. be defined based on map data, coordinates or the like, and/or by evaluating a distance between the at least one sensor and the at least one calibration sensor. The distance therebetween may for example be obtained by use of GNSS (global navigation satellite system) technology.

A "sensor reading" as used herein means a reading of a sensor when the sensor is collecting information relating to the property the sensor is measuring, wherein the sensor reading is performed during a sensor reading time period.

Calibration of a sensor as used herein means to calibrate the sensor by e.g. adjusting its output values with respect to a reference, wherein the reference is at least based on one or more measured values of the at least one calibration sensor.

Optionally, obtaining information about the refractory time period may comprise obtaining information about a refractory time period for the at least one sensor and a refractory time period for the at least one calibration sensor, and wherein the refractory time periods for the at least one sensor and the at least one calibration sensor are considered by delaying their sensor readings such that it is ensured that the sensor readings of the at least one sensor and the at least one calibration sensor are spatially and temporally aligned for the calibration. Thereby a further improved calibration may be achieved, taking the refractory time periods for both sensors into account. For example, the refractory time periods may be similar, but they may also be different. If the refractory time periods are different it may be required to delay the sensor readings differently such that it is ensured that the sensor readings of the at least one sensor and the at least one calibration sensor are spatially and temporally aligned for the calibration.

Optionally, the sensor reading/s may cease for at least the refractory time period/s prior to the arrival of the sensors in the predefined proximity zone. Thereby a further improved method may be achieved since it may be assured that the sensor readings can be initiated directly when the at least one sensor and the at least one calibration sensor are in the proximity zone. A risk of missing an opportunity to calibrate the at least one sensor may thereby be mitigated.

Optionally, the method may further comprise:
determining the proximity time period when the at least one sensor and the at least one calibration sensor are and/or will be in the predefined proximity zone by use of information about any one or a combination of relative speed, direction of movement and geolocation of the at least one sensor and the at least one calibration sensor. Thereby a more reliable determination of when the at least one sensor and the at least one calibration sensor are and/or will be in the predefined proximity zone may be achieved. Geolocation may for example be determined by use of GNSS technology as mentioned in the above. Of course, the skilled person will recognize that geolocation may additionally or alternatively be determined in a number of other ways, for example by triangulation by use of telecommunication signals, or by any other means, such as systems using LIDAR (Light Detection And Ranging), RADAR (Radio detection And Ranging), SONAR (SOund Navigation And Ranging), ultrasound waves etc. for identifying the geographical location of objects.

Optionally, at least one of the at least one sensor and the at least one calibration sensor may be mounted on a vehicle or vessel. Calibration of sensors as disclosed herein has been found the be especially advantageous for sensors which are mounted on vehicles or vessels, i.e. objects which are moving in an area or space. Such sensors may advantageously be calibrated in order to function properly, especially the type of sensors disclosed herein. Still optionally, the method may further comprise:
determining the proximity time period when the at least one sensor and the at least one calibration sensor are and/or will be in the predefined proximity zone by use of any one or a combination of:
information about a time table associated with the vehicle or vessel;
data indicative of a movement pattern of the vehicle or vessel.

Thereby, by using such information and/or data, a reliable determination of the proximity time period when the at least one sensor and the at least one calibration sensor are and/or will be in the predefined proximity zone can be achieved. For example, it has been found that a time table, such as a bus time table, may be used for this purpose. Such information may also advantageously be combined with other means for determining the proximity time period, thereby further improving the determination.

Optionally, the method may further comprise:
identifying a need for calibrating the at least one sensor based on at least one of the following:
a calibration schedule;
an analysis of previous sensor readings of the at least one sensor;
a determination that a predetermined threshold will be exceeded until a next possible opportunity to calibrate the at least one sensor, wherein the predetermined threshold is indicative of a lapsed time and/or a number of sensor readings after which the at least one sensor needs to be calibrated;
a comparison with a known sensor data pattern indicating that calibration is needed; and
a machine learning algorithm.

For example, by use of machine learning, the need for calibration can be identified in an improved manner. The machine learning may for example be based on previous sensor readings and/or known sensor data from other sources, and therefrom patterns, deviations etc. may be identified.

By identifying a need for calibrating the at least one sensor, it can be assured that the sensor needing calibration is actually calibrated when an opportunity to calibrate the sensor is given. In addition, identifying a need for calibration may also prevent any unnecessary calibration. Preventing unnecessary calibration may for example increase the sensors' service life, reduce energy consumption etc.

Optionally, the need for calibrating the at least one sensor may be identified based on an analysis of previous sensor readings of the at least one sensor, wherein the analysis comprises identifying a statistically significant increase in a number of outlying data points of the sensor readings. The analysis may in an embodiment be included in the above-mentioned machine learning algorithm.

Optionally, the at least one calibration sensor may be any one of:
the same type as the at least one sensor;
a reference sensor measuring the same property as the at least one sensor; and
a sensor for measuring another property than the at least one sensor, which other property can be used to calibrate the at least one sensor.

As such, the at least one calibration sensor may be any type of sensor which is suitable for the calibration. It has been realized that the at least one calibration sensor does not necessarily need to be of the same type, and may even not be configured to measure the same property. Thereby, an opportunity for calibration may appear more often, implying increased versatility.

Optionally, the method may further comprise:
determining when a plurality of sensors which require calibration will be in the predefined proximity zone; and
taking the sensor readings of the plurality of sensors and/or of the at least one calibration sensor such that it is ensured that a maximum number of the plurality of sensors will be calibrated.

Thereby, a further improved method may be achieved, allowing more sensors to be efficiently calibrated.

Optionally, the at least one sensor and/or the at least one calibration sensor may be one of the following:
a sensor measuring characteristics of sampled gases, liquids or particles, such as overall composition or concentration or directly measuring physical characteristics such as size, radiative or optical properties, etc.;
a sensor measuring electromagnetic parameters;
a temperature sensor;
a pressure sensor;
a humidity sensor.

For example, the at least one sensor and/or the at least one calibration sensor may be configured to measure $NO_x$ levels, $O_2$ levels, $CO_x$ levels and/or particle levels. Yet further, the at least one sensor and/or the at least one calibration sensor may be an air quality sensor.

Optionally, the at least one sensor may be part of an array of sensors located proximate each other, which array of sensors is calibrated according to the method disclosed herein. Still optionally, the at least one calibration sensor may be part of an array of calibration sensors located proximate each other, which array of calibration sensors is used to calibrate the at least one sensor according to the method disclosed herein.

According to a second aspect of the invention, the object is achieved by a system according to claim 12. Thus, a system for calibrating at least one sensor by use of at least one calibration sensor is provided. The system comprises the at least one sensor and the at least one calibration sensor, wherein the at least one sensor and the at least one calibration sensor are adapted to be moved relative each other during calibration, and wherein the system is configured to perform the steps of the method according to any one of the embodiments of the first aspect of the invention. Advantages and effects of the second aspect of the invention are largely analogous to the advantages and effects of the first aspect of the invention. It shall also be noted that all embodiments of the first aspect of the invention are applicable to and combinable with all embodiments of the second aspect of the invention, and vice versa.

Optionally, the system may comprise at least one control unit for performing the steps of the method as disclosed herein. The control unit is preferably an electronic control unit comprising processing circuitry for performing the method.

As such, according to another aspect of the disclosure, a computer program is disclosed, wherein the computer program comprises program code means for causing the at least one control unit to perform the steps of any one of the embodiments of the method as disclosed herein. According to a yet further aspect of the disclosure, a computer readable medium is disclosed, wherein the computer readable medium is carrying a computer program comprising program code means to cause the at least one control unit to perform the steps of any one of the embodiments of the method as disclosed herein.

According to a third aspect of the invention, the object is achieved by a first vehicle or vessel according to claim 13. Thus, a first vehicle or vessel is provided comprising at least one sensor which is configured to be calibrated by at least one calibration sensor which is remote from the first vehicle or vessel, wherein the first vehicle or vessel is part of the system according to any one of the embodiments of the second aspect of the invention, and/or wherein the first vehicle or vessel is configured to perform the method according to any one of the embodiments of the first aspect of the invention. Advantages and effects of the third aspect of the invention are largely analogous to the advantages and effects of the first and second aspects of the invention. It shall also be noted that all embodiments of the first and second aspects of the invention are applicable to and combinable with all embodiments of the third aspect of the invention, and vice versa. Optionally, the first vehicle or vessel may comprise at least one control unit as disclosed herein, and/or a computer program, computer readable medium as disclosed herein.

According to a fourth object of the invention, the object is achieved by a second vehicle or vessel comprising at least one calibration sensor for calibrating at least one sensor of another vehicle, wherein the second vehicle or vessel is part of the system according to any one of the embodiments of the second aspect of the invention. Advantages and effects of the fourth aspect of the invention are largely analogous to the advantages and effects of the first, second and third aspects of the invention. It shall also be noted that all embodiments of the first, second and third aspects of the invention are applicable to and combinable with all embodiments of the fourth aspect of the invention, and vice versa.

Optionally, the system according to the second aspect, the first vehicle or vessel according to the third aspect and/or the second vehicle or vessel according to the fourth aspect may further comprise means for wireless communication for communicating with another vehicle or vessel and/or with an offboard control system for vehicles or vessels. Such means may for example be based on telecommunication technology, such as 3G, 4G, 5G, wireless transfer via WiFi, Bluetooth etc. For example, the first vehicle or vessel may communicate wirelessly with the second vehicle or vessel in order to coordinate the sensor readings of the at least one sensor and the at least calibration sensor as disclosed herein. The communication may be a one-way communication or a two-way communication. Additionally, or alternatively, a one-way communication or a two-way communication may be established between an offboard control system and at least one of the first vehicle or vessel and the second vehicle or vessel. The offboard control system may for example be a cloud-based system and/or a remote central for coordinating the calibration.

The first vehicle or vessel and/or the second vehicle or vessel may be any type of vehicle, such as a truck, a bus, construction equipment, a marine vessel, a drone and a passenger car. The first and/or second vehicle or vessel may be propelled by any type of propulsion unit, such as a combustion engine, an electric motor or a combination of a combustion engine and an electric motor.

Further advantages and advantageous features of the invention are disclosed in the following description and in the dependent claims.

BRIEF DESCRIPTION OF THE DRAWINGS

With reference to the appended drawings, below follows a more detailed description of embodiments of the invention cited as examples.

In the drawings.

Figure 1:
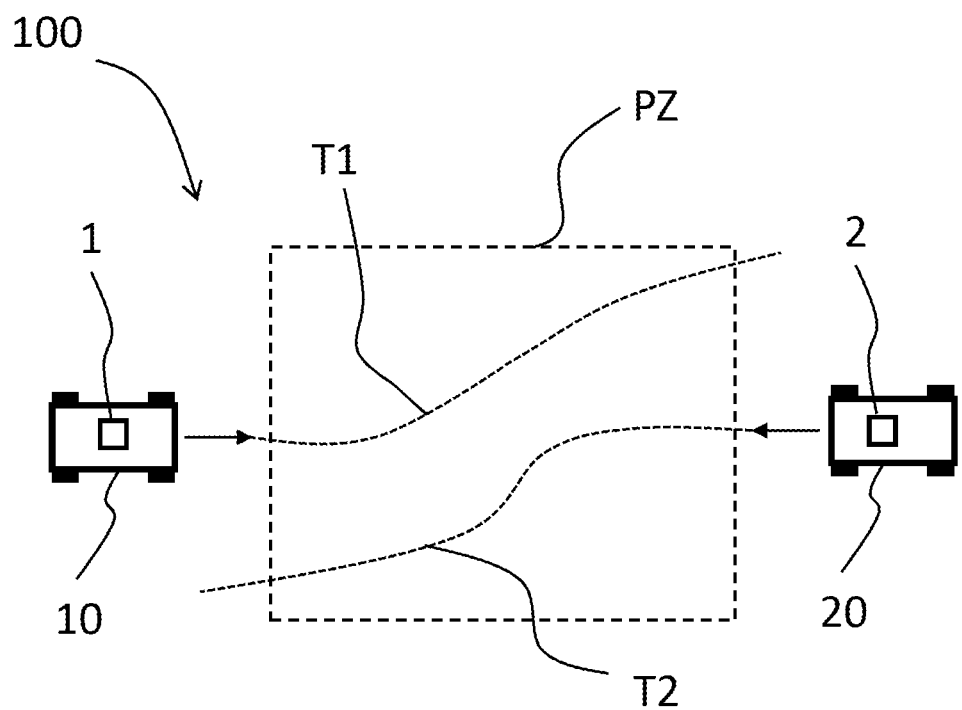
FIG. 1 is a schematic view of two vehicles which utilize an embodiment of the method according to the invention.

The drawings show diagrammatic exemplifying embodiments of the present disclosure and are thus not necessarily drawn to scale. It shall be understood that the embodiments shown and described are exemplifying and that the invention is not limited to these embodiments. It shall also be noted that some details in the drawings may be exaggerated in order to better describe and illustrate the particular embodiment. Like reference characters refer to like elements throughout the description, unless expressed otherwise.

DETAILED DESCRIPTION OF EXAMPLE EMBODIMENTS OF THE INVENTION

In FIG. 1, a first vehicle 10 and a second vehicle 20 are schematically illustrated from above. The first and second vehicles 10, 20 are here road vehicles comprising wheels. It shall however be noted, as already mentioned in the above, that the vehicles could be of any kind. It may even be a vessel for marine use or an aircraft, such as a drone, a helicopter or an airplane.

The first vehicle 10 comprises at least one sensor 1 and the second vehicle 20 comprises at least one calibration sensor 2. In this non-limiting example, the sensors 1, 2 are air quality sensors for measuring $NO_x$ levels, such as for measuring $NO_x$ levels in an urban area. Such sensors may require to be calibrated during use in order to provide accurate output values. Calibration may accordingly be performed one or more times during use of the at least one sensor 1. According to an embodiment, the at least one calibration sensor 2 may also need be calibrated. Therefore, the at least one calibration sensor 2 may be calibrated in a similar manner as the at least one sensor 1. Thus, according to a yet further example embodiment, the at least one sensor 1 and the at least one calibration sensor 2 are calibrated at the same time, by use of one another.

Figure 2:
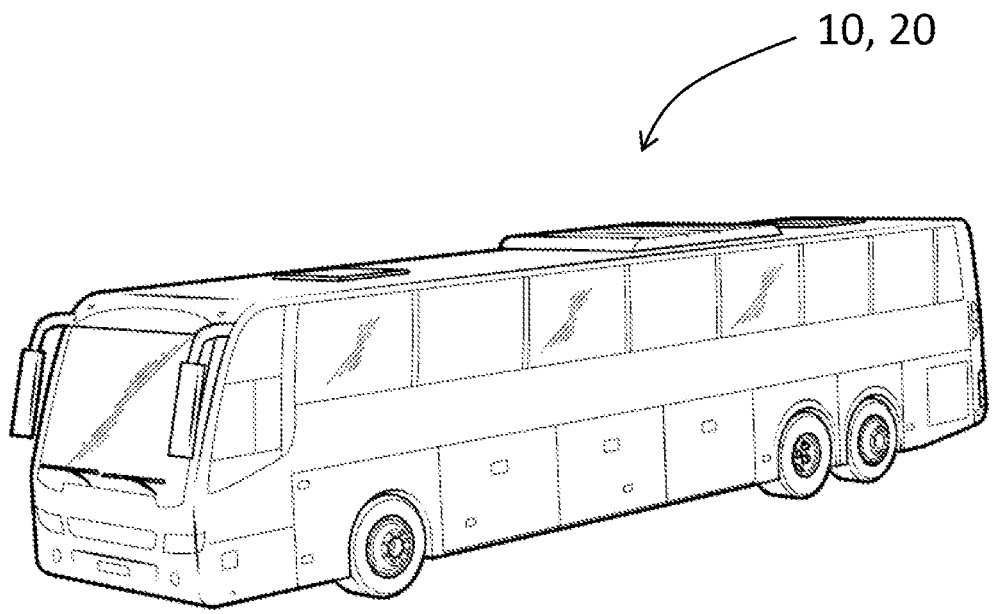
FIG. 2 is a perspective view of a first vehicle in the form of a bus according to an example embodiment of the invention.

FIG. 2 depicts a perspective view of a bus 10, 20. Accordingly, each vehicle 10, 20 in FIG. 1 may e.g. be a bus as shown in FIG. 2.

Figure 3:
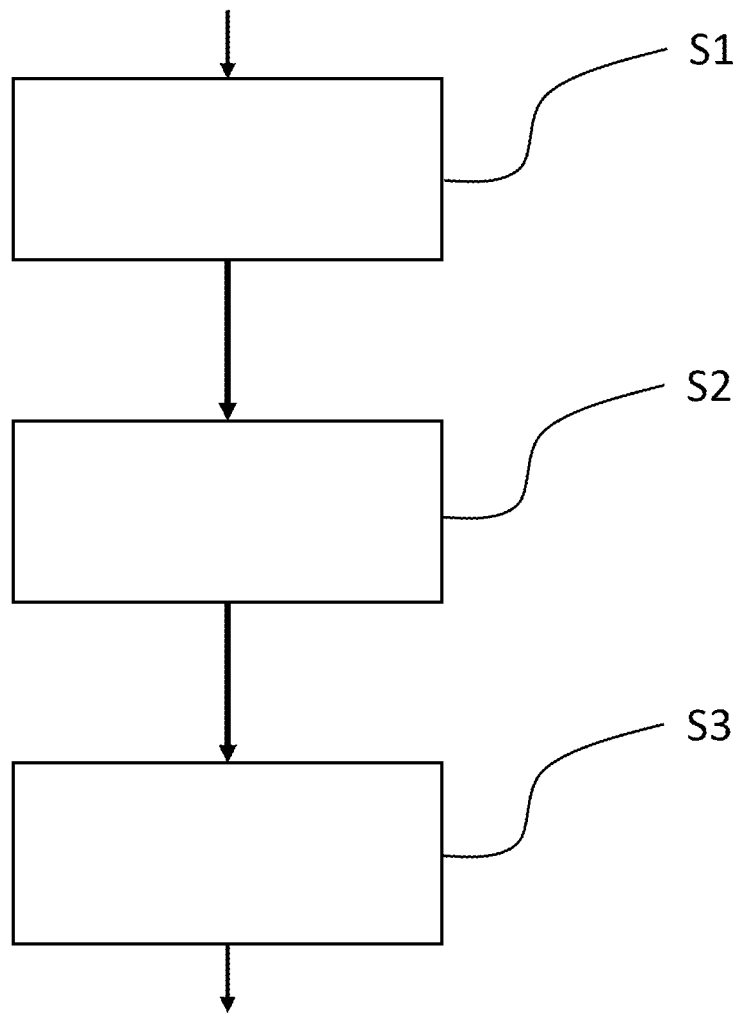
FIG. 3 is a flowchart of an example embodiment of a method according to the invention.

With respect to FIGS. 1-3, example embodiments of a method according to the invention will be described. FIG. 3 shows an example flowchart of the method.

The method is a method for calibrating e.g. the at least one sensor 1 by use of the at least one calibration sensor 2, wherein the at least one sensor 1 and the at least one calibration sensor 2 are moving relative each other during calibration. In the shown embodiments, the at least one sensor 1 and the at least one calibration sensor are moving since the vehicles 10 and 20 are moving. The vehicles 10, 20 are here moving along respective trajectories, T1, T2. The trajectories T1, T2 define travelling paths for the vehicles 10, 20.

The method comprises:

S1: obtaining information indicative of a proximity time period pt when the at least one sensor 1 and the at least one calibration sensor 2 are and/or will be in a predefined proximity zone PZ of each other for a time period which is sufficient for calibration.

The predefined proximity zone PZ is here indicated by dashed lines in FIG. 1. As mentioned in the above, the predefined proximity zone PZ may e.g. be defined by a maximum allowed distance between the at least one sensor 1 and the at least one calibration sensor 2. Purely by way of example, the maximum allowed distance may be 100 metres (m) from each other. Of course, the maximum allowed distance is highly dependent on the specific situation, type of sensor etc. As such, this example is merely one example of many. A time period which is sufficient for calibration may be determined in e.g. minutes or seconds (s), such as 5, 10, 15 or 20 s. Of course, this time period is also highly dependent on the specific situation, type of sensor etc.

The method further comprises:

S2: obtaining information about a refractory time period rs, rc for at least one of the at least one sensor 1 and the at least one calibration sensor 2, the refractory time period defining a time period between two consecutive sensor readings in which the sensor, 1 and/or 2, is unable to take a sensor reading; and S3: calibrating the at least one sensor 1 by a sensor reading of the at least one sensor 1 and a sensor reading of the at least one calibration sensor 2, which sensor readings are taken when they are in the predefined proximity zone PZ, wherein the refractory time period rs, rc for the at least one of the at least one sensor 1 and the at least one calibration sensor 2 is considered by delaying its sensor reading such that it is ensured that the sensor readings of the at least one sensor 1 and the at least one calibration sensor 2 are spatially and temporally aligned for the calibration.

For example, the sensor reading/s may cease for at least the refractory time period/s rs, rc prior to the arrival of the sensors 1, 2 in the predefined proximity zone PZ.

Obtaining information about the refractory time period rs, rc may comprise obtaining information about a refractory time period rs for the at least one sensor 1 and a refractory time period rc for the at least one calibration sensor 2, and wherein the refractory time periods rs, rc for the at least one sensor 1 and the at least one calibration sensor 2 are considered by delaying their sensor readings such that it is ensured that the sensor readings of the at least one sensor 1 and the at least one calibration sensor 2 are spatially and temporally aligned for the calibration.

The method may further comprise:

determining the proximity time period pt when the at least one sensor 1 and the at least one calibration sensor 2 are and/or will be in the predefined proximity zone PZ by use of information about any one or a combination of relative speed, direction of movement and geolocation of the at least one sensor 1 and the at least one calibration sensor 2. For example, by using information about the trajectories T1, T2 it may be possible to determine the proximity time period pt when the at least one sensor 1 and the at least one calibration sensor 2 are and/or will be in the predefined proximity zone PZ.

Additionally, or alternatively, the method may further comprise:

determining the proximity time period pt when the at least one sensor 1 and the at least one calibration sensor 2 are and/or will be in the predefined proximity zone PZ by use of any one or a combination of:

information about a time table associated with the vehicles 10, 20;

data indicative of a movement pattern of the vehicle 10, 20 or vessel.

Accordingly, the data in this example may be data relating to the trajectories T1, T2. In addition, the time table may for example be a time table for the bus 10, 20 as shown in FIG. 2.

The method may further comprise:

identifying a need for calibrating the at least one sensor 1 based on at least one of the following:

a calibration schedule;

an analysis of previous sensor readings of the at least one sensor 1;

a determination that a predetermined threshold will be exceeded until a next possible opportunity to calibrate the at least one sensor 1, wherein the predetermined threshold is indicative of a lapsed time and/or a number of sensor readings after which the at least one sensor 1 needs to be calibrated;

a comparison with a known sensor data pattern indicating that calibration is needed; and a machine learning algorithm.

Additionally, or alternatively, the need for calibrating the at least one sensor 1 may be identified based on an analysis of previous sensor readings of the at least one sensor 1, wherein the analysis comprises identifying a statistically significant increase in a number of outlying data points of the sensor readings.

As mentioned in the above, the example in FIG. 1 relates to air quality sensors. However, the at least one calibration sensor 2 may be any one of:

the same type as the at least one sensor 1;

a reference sensor measuring the same property as the at least one sensor 1; and a sensor for measuring another property than the at least one sensor, which other property can be used to calibrate the at least one sensor 1.

An example of another property may be that the at least one calibration sensor 2 is a temperature sensor, and that the at least one sensor 1 is an air quality sensor measuring $NO_x$ levels. As such, the at least one sensor 1 may be calibrated by use of the temperature information measured by the at least one calibration sensor 2 when being in the predefined proximity zone PZ while also the at least one sensor 1 is in the predefined proximity zone PZ.

The method may further comprise:
determining when a plurality of sensors which require calibration will be in the predefined proximity zone PZ; and
taking the sensor readings of the plurality of sensors and/or of the at least one calibration sensor 2 such that it is ensured that a maximum number of the plurality of sensors will be calibrated. For example, more than two vehicles with sensors may be in the predefined proximity zone PZ.

According to the second aspect of the invention, the at least one sensor 1 and the at least one calibration sensor 2 may form part of a system 100, wherein the at least one sensor 1 and the at least one calibration sensor 2 are adapted to be moved relative each other during calibration. Accordingly, the system 100 may be configured to perform the steps of the method according to any one of the preceding claims. For example, the vehicle 10 and/or the vehicle 20 may comprise at least one control unit (not shown), wherein the at least one control unit comprises hardware and/or software for performing the method as disclosed herein.

According to a yet further aspect, the first vehicle 10 may be configured to perform the method as disclosed herein, e.g. by use of the aforementioned control unit.

The first vehicle 10 and/or the second vehicle 20 preferably comprises means for wireless communication for communicating with the other vehicle and/or with an offboard control system (not shown) for vehicles.

It is to be understood that the present invention is not limited to the embodiments described above and illustrated in the drawings; rather, the skilled person will recognize that many changes and modifications may be made within the scope of the appended claims.

The invention claimed is:

1. A computer-implemented method for calibrating at least one sensor by use of at least one calibration sensor, wherein the at least one sensor and the at least one calibration sensor are moving relative each other during calibration, the method comprising:
obtaining information indicative of a proximity time period when the at least one sensor and the at least one calibration sensor are and/or will be in a predefined proximity zone of each other for a time period which is sufficient for calibration;
obtaining information about a refractory time period for at least one of the at least one sensor and the at least one calibration sensor, the refractory time period defining a time period between two consecutive sensor readings in which the sensor is unable to take a sensor reading;
calibrating the at least one sensor by a sensor reading of the at least one sensor and a sensor reading of the at least one calibration sensor, which sensor readings are taken when they are in the predefined proximity zone, wherein the refractory time period for the at least one of the at least one sensor and the at least one calibration sensor is considered by delaying its sensor reading such that it is ensured that the sensor readings of the at least one sensor and the at least one calibration sensor are spatially and temporally aligned for the calibration.

2. The method according to claim 1, wherein obtaining information about the refractory time period comprises obtaining information about a refractory time period for the at least one sensor and a refractory time period for the at least one calibration sensor, and wherein the refractory time periods for the at least one sensor and the at least one calibration sensor are considered by delaying their sensor readings such that it is ensured that the sensor readings of the at least one sensor and the at least one calibration sensor are spatially and temporally aligned for the calibration.

3. The method according to claim 1, wherein the sensor reading/s cease for at least the refractory time period/s prior to the arrival of the sensors in the predefined proximity zone.

4. The method according to claim 1, further comprising:
determining the proximity time period when the at least one sensor and the at least one calibration sensor are and/or will be in the predefined proximity zone by use of information about any one or a combination of relative speed, direction of movement and geolocation of the at least one sensor and the at least one calibration sensor.

5. The method according to claim 1, wherein at least one of the at least one sensor and the at least one calibration sensor is mounted on a vehicle or vessel.

6. The method according to claim 5, further comprising:
determining the proximity time period when the at least one sensor and the at least one calibration sensor are and/or will be in the predefined proximity zone by use of any one or a combination of:
information about a time table associated with the vehicle or vessel;
data indicative of a movement pattern of the vehicle or vessel.

7. The method according to claim 1, further comprising:
identifying a need for calibrating the at least one sensor based on at least one of the following:
a calibration schedule;
an analysis of previous sensor readings of the at least one sensor;
a determination that a predetermined threshold will be exceeded until a next possible opportunity to calibrate the at least one sensor, wherein the predetermined threshold is indicative of a lapsed time and/or a number of sensor readings after which the at least one sensor needs to be calibrated;
a comparison with a known sensor data pattern indicating that calibration is needed; and
a machine learning algorithm.

8. The method according to claim 7, wherein the need for calibrating is identified based on an analysis of previous sensor readings of the at least one sensor, wherein the analysis comprises identifying a statistically significant increase in a number of outlying data points of the sensor readings.

9. The method according to claim 1, wherein the at least one calibration sensor is any one of:
the same type as the at least one sensor;
a reference sensor measuring the same property as the at least one sensor; and
a sensor for measuring another property than the at least one sensor, which other property can be used to calibrate the at least one sensor.

10. The method according to claim 1, further comprising:
determining when a plurality of sensors which require calibration will be in the predefined proximity zone; and taking the sensor readings of the plurality of sensors and/or of the at least one calibration sensor such that it is ensured that a maximum number of the plurality of sensors will be calibrated.

11. The method according to claim 1, wherein the at least one sensor and/or the at least one calibration sensor is one of the following:
- a sensor measuring characteristics of sampled gases, liquids or particles, such as overall composition or concentration or directly measuring physical characteristics such as size, radiative or optical properties, etc.;
- a sensor measuring electromagnetic parameters;
- a temperature sensor;
- a pressure sensor;
- a humidity sensor.

12. A system for calibrating at least one sensor by use of at least one calibration sensor, the system comprising the at least one sensor and the at least one calibration sensor, wherein the at least one sensor and the at least one calibration sensor are adapted to be moved relative each other during calibration, and wherein the system is configured to perform the steps of the method according to claim 1.

13. A first vehicle or vessel comprising of the system according to claim 12 and including at least one sensor which is configured to be calibrated by at least one calibration sensor which is remote from the first vehicle or vessel.

14. A second vehicle or vessel comprising the system according to claim 12 and including at least one calibration sensor for calibrating at least one sensor of another vehicle.

15. The system according to claim 12 further comprising means for wireless communication for communicating with another vehicle or vessel and/or with an offboard control system for vehicles or vessels.

\* \* \* \* \*